US010926246B2

(12) United States Patent
Han et al.

(10) Patent No.: US 10,926,246 B2
(45) Date of Patent: Feb. 23, 2021

(54) METHOD OF PREPARING CATALYST FOR OXIDATIVE DEHYDROGENATION

(71) Applicant: LG CHEM, LTD., Seoul (KR)

(72) Inventors: Jun Kyu Han, Daejeon (KR); Dong Hyun Ko, Daejeon (KR); Kyong Yong Cha, Daejeon (KR); Myung Ji Suh, Daejeon (KR); Sun Hwan Hwang, Daejeon (KR); Seong Min Kim, Daejeon (KR)

(73) Assignee: LG CHEM, LTD., Seoul (KR)

(*) Notice: Subject to any disclaimer, the term of this patent is extended or adjusted under 35 U.S.C. 154(b) by 0 days.

(21) Appl. No.: 15/744,721

(22) PCT Filed: Mar. 15, 2017

(86) PCT No.: PCT/KR2017/002778
§ 371 (c)(1),
(2) Date: Jan. 12, 2018

(87) PCT Pub. No.: WO2017/160071
PCT Pub. Date: Sep. 21, 2017

(65) Prior Publication Data
US 2018/0207621 A1 Jul. 26, 2018

(30) Foreign Application Priority Data

Mar. 18, 2016 (KR) .................. 10-2016-0032647
Mar. 10, 2017 (KR) .................. 10-2017-0030425

(51) Int. Cl.
*B01J 23/745* (2006.01)
*B01J 37/03* (2006.01)
(Continued)

(52) U.S. Cl.
CPC .......... *B01J 23/745* (2013.01); *B01J 21/005* (2013.01); *B01J 21/10* (2013.01); *B01J 23/005* (2013.01);
(Continued)

(58) Field of Classification Search
CPC ...................................... B01J 23/745
(Continued)

(56) References Cited

U.S. PATENT DOCUMENTS 3,595,810 A * 7/1971 Kehl ...................... B01J 23/862
502/307
2010/0121123 A1 5/2010 Chung et al.
(Continued)

FOREIGN PATENT DOCUMENTS

CN 1184705 6/1998
CN 101674883 3/2010
(Continued)

OTHER PUBLICATIONS

Phase Cooperation between ZnFe2O4 and alpha-Fe2O3 phases of Ferrite Catalysts in the Oxidative Dehyfrogenation of n-Butenes Mingqian Zhang et al. J. Chem. Soc. Faraday Trans. V88 Issue (4), pp. 637-644 (Year: 1992).*
(Continued)

*Primary Examiner* — Douglas B Call
(74) *Attorney, Agent, or Firm* — Dentons US LLP

(57) ABSTRACT

The present invention relates to a method of preparing a catalyst for oxidative dehydrogenation. More particularly, the present invention provides a method of preparing a catalyst for oxidative dehydrogenation providing superior selectivity and yield for a conjugated diene according to oxidative dehydrogenation by constantly maintaining pH of
(Continued)

a coprecipitation solution using a drip-type double precipitation method to adjust an α-iron oxide content in a catalyst in a predetermined range.

7 Claims, 3 Drawing Sheets

(51) Int. Cl.

| | |
|---|---|
| *B01J 23/78* | (2006.01) |
| *B01J 23/80* | (2006.01) |
| *B01J 23/75* | (2006.01) |
| *B01J 23/889* | (2006.01) |
| *B01J 27/053* | (2006.01) |
| *B01J 27/10* | (2006.01) |
| *B01J 27/25* | (2006.01) |
| *B01J 35/02* | (2006.01) |
| *B01J 35/10* | (2006.01) |
| *B01J 37/00* | (2006.01) |
| *B01J 21/00* | (2006.01) |
| *B01J 21/10* | (2006.01) |
| *B01J 35/00* | (2006.01) |
| *B01J 37/08* | (2006.01) |
| *C07C 5/48* | (2006.01) |
| *B01J 23/00* | (2006.01) |
| *B01J 23/85* | (2006.01) |

(52) U.S. Cl.
CPC .............. *B01J 23/75* (2013.01); *B01J 23/78* (2013.01); *B01J 23/80* (2013.01); *B01J 23/85* (2013.01); *B01J 23/8892* (2013.01); *B01J 27/053* (2013.01); *B01J 27/10* (2013.01); *B01J 27/25* (2013.01); *B01J 35/0006* (2013.01); *B01J 35/023* (2013.01); *B01J 35/1009* (2013.01); *B01J 37/009* (2013.01); *B01J 37/031* (2013.01); *B01J 37/088* (2013.01); *C07C 5/48* (2013.01); *C07C 2523/745* (2013.01); *C07C 2523/80* (2013.01)

(58) Field of Classification Search
USPC .......................................... 502/300
See application file for complete search history.

(56) References Cited

U.S. PATENT DOCUMENTS

| | | | |
|---|---|---|---|
| 2012/0059208 A1* | 3/2012 | Mamedov | B01J 23/80 585/625 |
| 2013/0158325 A1 | 6/2013 | Kwon et al. | |

FOREIGN PATENT DOCUMENTS

| | | |
|---|---|---|
| CN | 103025425 | 4/2013 |
| CN | 103055871 | 4/2013 |
| CN | 103079695 | 5/2013 |
| CN | 103102238 | 5/2013 |
| CN | 104001533 | 8/2014 |
| CN | 105236454 | 1/2016 |
| EP | 3222347 | 9/2017 |
| EP | 3292910 A1 | 3/2018 |
| EP | 3308854 | 4/2018 |
| JP | 2015167886 | 9/2015 |
| KR | 10-0847206 | 7/2008 |
| KR | 10-2012-0009687 | 2/2012 |
| WO | 2009045002 | 4/2009 |

OTHER PUBLICATIONS

Customer Manual—Aqua Ammonia—Tanner Industries pp. 1-9 Downloaded Dec. 31, 2019 (Year: 1998).*
PH of common Acids and Bases Aqion, pp. 1-5 Downloaded Dec. 31, 2019 (Year: 2019).*
Sigma-Aldrich Product Information Ammonium Hydroxide downloaded Jun. 16, 2020, pp. 1 (Year: 2003).*
Office Action of Chinese Patent Office in Appl'n No. 201780002342.9 dated Nov. 4, 2019.
Toledo et al., "A Magnetically Ordered Non-Stoichiometric Zinc Ferrite for the Oxidative Dehydrogenation Reacions," Mat. Res. Soc. Symp. Proc. 676: Y3.5.1-5.6 (2001).
Toledo et al., "Oxidative dehydrogenation of 1-butene over Zn—Al ferrites," Journal of Molecular Catalysis A: Chemical 125: 53-62 (1997).
Gibson et al., "Oxidative Dehydrogenation of Butenes over Magnesium Ferrite," Journal of Catalysis 41: 431-439 (1976).
Office Action of European Patent Office in Appl'n No. 17766972.8 dated Aug. 9, 2019.
Lee et al., "Preparation of ZnFe2O4 Catalysts by a Co-precipitation Method Using Aqueous Buffer Solution and Their Catalytic Activity for Oxidative Dehydrogenation of n-Butene to 1,3-Butadiene," Catal. Lett. 122: 281-286 (2008).
Lee et al., "Effect of pH in the preparation of ZnFeO4 for oxidative dehydrogenation of n-butene to 1,3 butadiene: Correlation between catalytic performance and surface acidity of ZnFe204," Catalysis Communications 9: 1137-1142 (2008).
Jung et al., "Oxidative Dehydrogenation of C4 Raffinate-3 to 1,3-Butadiene in a Dual-bed Reaction System Comprising ZnFe2O4 and Co9Fe3Bi1Mo12O51 Catalysts: A Synergistic Effect of ZnFe2O4 and Co9Fe3Bi1Mo12O51 Catalysts," Catal. Lett. 123: 239-245 (2008).

* cited by examiner

[FIG. 1]
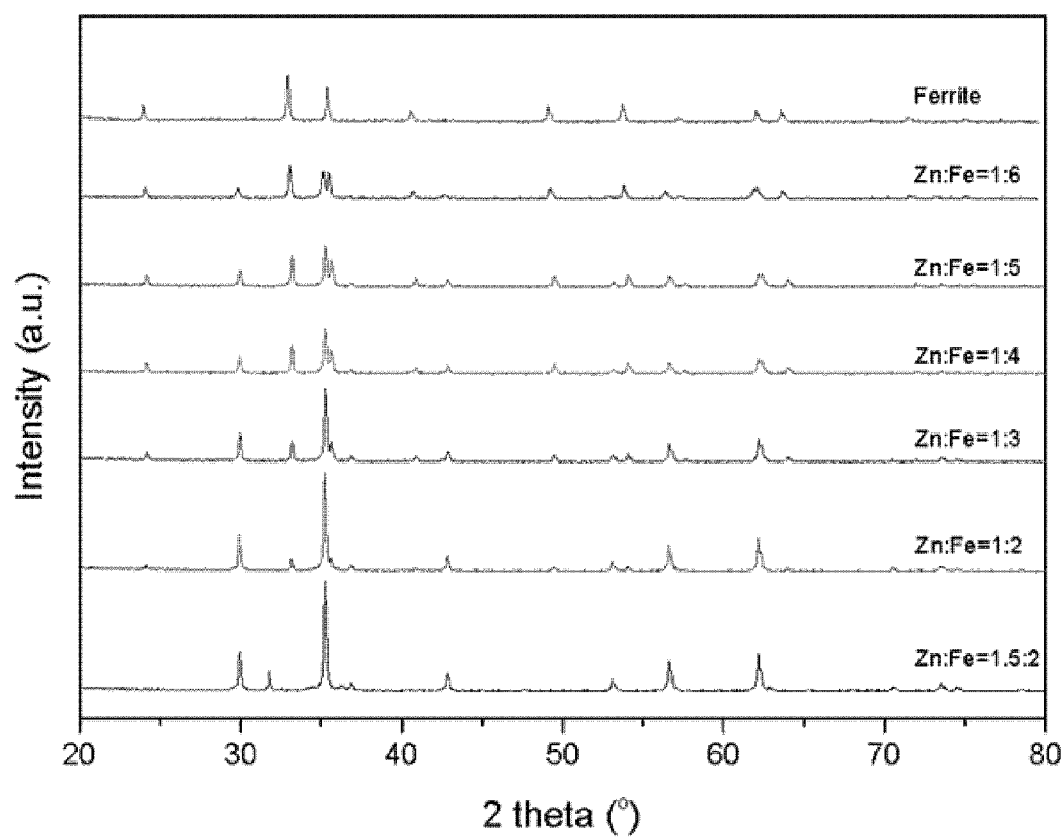

【FIG. 2】
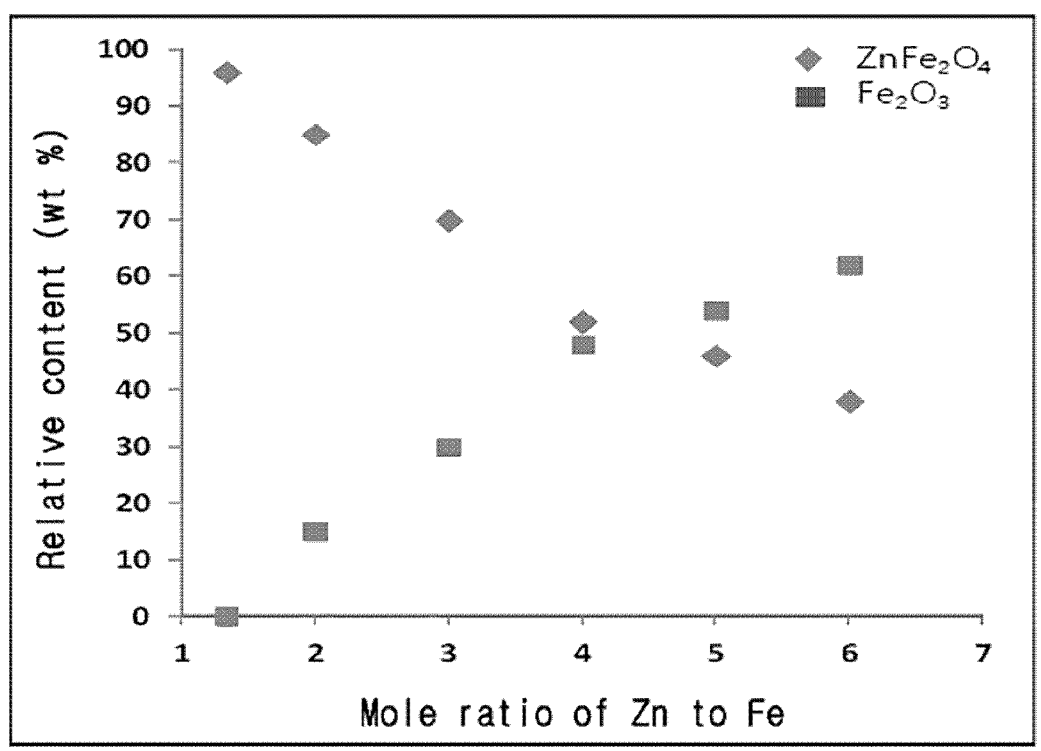

[FIG. 3]
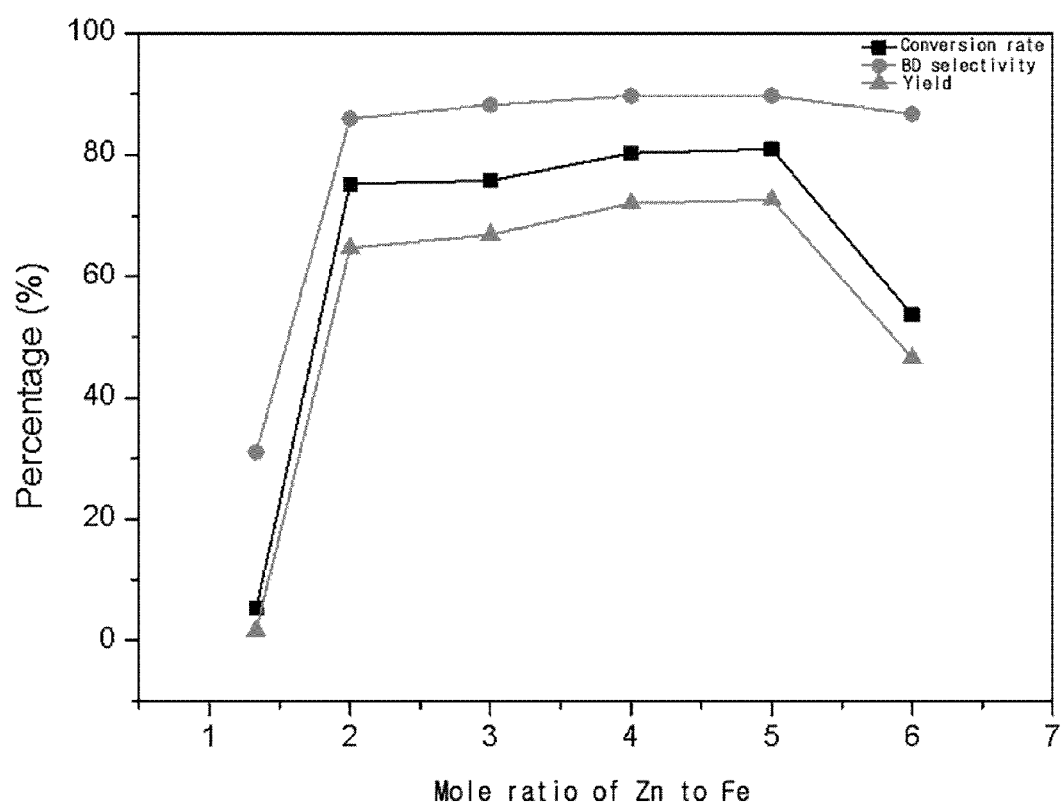

METHOD OF PREPARING CATALYST FOR OXIDATIVE DEHYDROGENATION

CROSS-REFERENCE TO RELATED APPLICATIONS

This application is a National Stage Application of International Application No. PCT/KR2017/002778 filed on Mar. 15, 2017, which claims the priority to and the benefit of Korean Patent Application No. 10-2016-0032647, filed on Mar. 18, 2016, and Korean Patent Application No. 10-2017-0030425, filed on Mar. 10, 2017, in the Korean Intellectual Property Office, all of which are incorporated herein in their entirety by reference for all purposes as if fully set forth herein.

TECHNICAL FIELD

The present invention relates to a method of preparing a catalyst for oxidative dehydrogenation. More particularly, the present invention relates to a method of preparing a catalyst for oxidative dehydrogenation providing superior selectivity and yield for a conjugated diene according to oxidative dehydrogenation by constantly maintaining pH of a coprecipitation solution using a drip-type double precipitation method to adjust an α-iron oxide content in a catalyst in a predetermined range.

BACKGROUND ART

Demand for 1,3-butadiene, which is an intermediate in petrochemical products, and the value thereof are gradually increasing throughout the world. To produce such 1,3-butadiene, methods, such as naphtha cracking, direct butene dehydrogenation, and oxidative dehydrogenation of butene, have been used. However, in the case of naphtha cracking, energy consumption is high due to high reaction temperature. In addition, since naphtha cracking is not a process specifically designed for production of 1,3-butadiene production, other basic oils, other than 1,3-butadiene, are disadvantageously produced as surplus products. Meanwhile, direct dehydrogenation of normal-butene is thermodynamically unfavorable. In addition, since direct dehydrogenation of normal-butene is an endothermic reaction, high-temperature and low-pressure conditions are required to produce 1,3-butadiene in a high yield. Accordingly, direct dehydrogenation of normal-butene is not suitable as a commercial process for producing 1,3-butadiene.

Meanwhile, since, in the case of oxidative dehydrogenation of butene wherein butene reacts with oxygen in the presence of a metal oxide catalyst to generate 1,3-butadiene and water, stable water is generated and oxidative dehydrogenation of butene is thermodynamically advantageous. In addition, since oxidative dehydrogenation of butene is an exothermic reaction unlike direct dehydrogenation of butene, oxidative dehydrogenation of butene may produce 1,3-butadiene in a high yield even at low reaction temperature, compared to direct dehydrogenation of butene. In addition, since oxidative dehydrogenation of butene does not require additional heat supply, oxidative dehydrogenation of butene may be considered an effective production process that produces only 1,3-butadiene and thus satisfies demand for 1,3-butadiene.

Metal oxide catalysts are generally synthesized by a precipitation method. In the precipitation method, pH, such as the pH of an aqueous metal oxide precursor solution, the pH of a basic aqueous solution, and the pH of a coprecipitate, acts as important synthesis parameters. Since such synthesis parameter affects the phase of a coprecipitate and a catalyst prepared by the precipitation method affects the selectivity and yield of 1,3-butadiene depending upon the phase of the coprecipitate, a technology of stably maintaining pH during synthesis is very important. Therefore, there is a need for a catalyst preparation method of more stably maintaining pH during preparation of a metal oxide catalyst according to a precipitation method.

Related Art Document (Patent Document 1) JP2015-167886 A

DISCLOSURE

Technical Problem

Therefore, the present invention has been made in view of the above problems, and it is one object of the present invention to provide a method of preparing a catalyst for oxidative dehydrogenation. More particularly, the present invention relates to a method of preparing a catalyst for oxidative dehydrogenation providing superior selectivity and yield for a conjugated diene according to oxidative dehydrogenation by constantly maintaining pH of a coprecipitation solution using a drip-type double precipitation method to adjust an α-iron oxide content in a catalyst in a predetermined range.

The above and other objects can be accomplished by the present disclosure described below.

Technical Solution

In accordance with one aspect of the present invention, provided is a method of preparing a catalyst for oxidative dehydrogenation, the method including (a) a step of preparing an aqueous precursor solution by dissolving a trivalent cation iron (Fe) precursor and a divalent cation metal (A) precursor in water in a mole ratio (Fe/A) of 2 to 10; (b) a step of constantly maintaining pH of a coprecipitation solution by, when the aqueous precursor solution is fed dropwise into a coprecipitation tank in which a basic aqueous solution is prepared, feeding a basic aqueous solution identical to or different from the basic aqueous solution dropwise along with the aqueous precursor solution; and (c) a step of obtaining a coprecipitate by filtering the coprecipitation solution.

Advantageous Effects

As apparent from the fore-going, the present invention advantageously provides a method of preparing a catalyst for oxidative dehydrogenation. More particularly, the present invention relates to a method of preparing a catalyst for oxidative dehydrogenation providing superior selectivity and yield for a conjugated diene according to oxidative dehydrogenation by constantly maintaining pH of a coprecipitation solution using a drip-type double precipitation method to adjust an α-iron oxide content in a catalyst in a predetermined range.

DESCRIPTION OF DRAWINGS

FIG. 1 illustrates XRD (X-ray Diffraction) data of a catalyst prepared according to each of Examples 1 to 5 of the present invention and Comparative Example 2.

FIG. 2 is a graph illustrating a relative content (% by weight) with respect to a phase of a catalyst prepared according to each of Examples 1 to 5 of the present invention and Comparative Example 2.

FIG. 3 is a graph illustrating butene conversion rate, butadiene selectivity, and yield when butadiene is prepared using a catalyst prepared according to each of Examples 1 to 5 of the present invention and Comparative Example 2.

BEST MODE

Hereinafter, the present invention is described in detail.

The present inventors confirmed that, when an aqueous metal oxide precursor solution and a basic aqueous solution are dually fed dropwise into a coprecipitation tank containing a basic aqueous solution that is adjusted to have a specific pH so as to prepare a metal oxide catalyst for oxidative dehydrogenation by a precipitation method, pH of a coprecipitate is more stably controlled and thus a phase of a metal oxide catalyst prepared from the coprecipitate is controlled, whereby selectivity and yield of conjugated diene are improved. Based on this finding, the present invention has been completed.

Hereinafter, a method of preparing a catalyst for oxidative dehydrogenation according to the present invention is described in detail.

The method of preparing a catalyst for oxidative dehydrogenation includes (a) a step of preparing an aqueous precursor solution by dissolving a trivalent cation iron (Fe) precursor and a divalent cation metal (A) precursor in water in a mole ratio (Fe/A) of 2 to 10; (b) a step of constantly maintaining pH of a coprecipitation solution by, when the aqueous precursor solution is fed dropwise into a coprecipitation tank in which a basic aqueous solution is prepared, feeding a basic aqueous solution identical to or different from the basic aqueous solution dropwise along with the aqueous precursor solution; and (c) a step of obtaining a coprecipitate by filtering the coprecipitation solution.

The water may be, for example, distilled water or purified water, but is preferably distilled water.

The trivalent cation iron (Fe) precursor and the divalent cation metal (A) precursor of step (a) are not specifically limited so long as they are generally used in the art. For example, a metal salt including the trivalent cation iron (Fe) precursor and divalent cation metal (A) precursor ingredients may be used. For a specific example, a nitrate, ammonium salt, sulfate, or chloride of the metal ingredient may be used. Preferably, a chloride or nitrate thereof is used.

The divalent cation metal (A) may be, for example, one or more selected from the group consisting of divalent cation metals. As a particular example, the divalent cation metal (A) may be one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co). Preferably, the divalent cation metal (A) is one or more selected from the group consisting of zinc (Zn), magnesium (Mg), manganese (Mn), and cobalt (Co). More preferably, the divalent cation metal (A) is zinc (Zn) or manganese (Mn).

The trivalent cation iron (Fe) precursor and the divalent cation metal (A) precursor may be included, for example, in a mole ratio (Fe/A) of 2 to 10, 2 to 6, or 2 to 5 with respect to the aqueous precursor solution. Within this range, an α-iron oxide content in a catalyst may be controlled in a predetermined range, whereby selectivity and yield of a conjugated diene according to oxidative dehydrogenation become superior.

The aqueous precursor solution may have, for example, pH of 6 to 12, 6 to 10, or 8 to 10. Within this range, high activity and yield to prepare 1,3-butadiene may be obtained.

The aqueous precursor solution may have a concentration of 5% by weight to 10% by weight, 5% by weight to 8% by weight, or 6% by weight to 7% by weight. Within this range, reactivity of a catalyst for oxidative dehydrogenation may be improved.

The aqueous precursor solution may be prepared, for example, by dissolving 4% by weight or more and less than 10% by weight, 4% by weight to 7% by weight, or 4.5 to 6.5% by weight of a trivalent cation iron (Fe) precursor and 0.5% by weight or more and less than 10% by weight, 0.5% by weight to 6.5% by weight, or 0.5 to 6.2% by weight of a divalent cation metal precursor in greater than 80% by weight and 95.5% by weight or less, 86.5% by weight to 95.5% by weight, or 87.3% by weight to 95.0% by weight of distilled water.

The aqueous precursor solution may have, for example, pH of 0 to 4, 1 to 3, or 1 to 2. Within this range, desired active ingredients may be stably generated during synthesis of a catalyst.

In an embodiment, the basic aqueous solution in the coprecipitation tank and the basic aqueous solution added dropwise to the coprecipitation tank in step b may be aqueous solutions having the same concentration and pH or different concentrations or pHs, or may be different aqueous basic solutions. In a particular embodiment, the basic aqueous solutions may be respectively one or more selected from the group consisting of potassium hydroxide, ammonium carbonate, ammonium hydrogen carbonate, an aqueous sodium hydroxide solution, sodium carbonate, and an aqueous ammonia solution. Preferably, the basic aqueous solutions are aqueous ammonia solutions. In this case, a particle size of the catalyst is large, a phase thereof meets the objectives of the present invention, and a washing process may be easily performed.

The pH of each of the basic aqueous solutions may be, for example, greater than 8 and less than 11, 9 to 10, or 9 to 9.5. Within this range, an α-iron oxide content in a catalyst may be controlled in a predetermined range, whereby selectivity and yield of a conjugated diene according to oxidative dehydrogenation become superior.

Each of the basic aqueous solutions may have, for example, a concentration of 10 to 50% by weight, 15 to 40% by weight, or 25 to 30% by weight.

The basic aqueous solution added dropwise, which is provided to constantly maintain the pH of a coprecipitation solution changed due to the aqueous precursor solution added dropwise to a coprecipitation tank, might not be added dropwise, may be added dropwise with the aqueous precursor solution, or may be added alone, within a range within which the pH of the coprecipitation solution is constantly maintained.

In an embodiment, the aqueous precursor solution and the basic aqueous solution may be respectively added dropwise from separate outlets. In this case, the pH of a coprecipitation solution changed due to the aqueous precursor solution added dropwise to the coprecipitation tank may be constantly maintained by controlling a dropwise-added amount of the basic aqueous solution.

The aqueous precursor solution may be added to the coprecipitation tank dropwise at a rate of 20 g/min or more, 20 g/min to 50 g/min, or 40 g/min or more to 50 g/min. Within this range, selectivity and yield of butadiene according to oxidative dehydrogenation become superior.

The pH of the coprecipitation solution in step b may be, for example, greater than 8 and less than 11, 9 to 10, or 9 to 9.5. Within this range, an α-iron oxide content in a catalyst may be controlled within a predetermined range, whereby selectivity and yield of a conjugated diene according to oxidative dehydrogenation become superior.

Step b may further include, for example, a step of stirring a coprecipitation solution to which dropwise-addition of the aqueous precursor solution is completed. In this case, coprecipitation of the precursor in a coprecipitation solution may be sufficiently accomplished.

The stirring may be carried out, for example, for 30 minutes to 3 hours, 30 minutes to 2 hours, or 30 minutes to 1 hour and 30 minutes.

The filtering in step (c) is not specifically limited so long as it is performed by a filtration method generally used in the art. In an embodiment, the filtering may be performed by a vacuum filtration method. In a particular embodiment, the filtering may be performed by a method of performing filtration under reduced pressure by means of a vacuum pump. In this case, washing effect and catalyst separation effect from moisture may be exhibited.

In an embodiment, the method of preparing a catalyst for oxidative dehydrogenation may further include a step of drying; firing; or drying and firing the coprecipitate obtained by step (c).

The filtered coprecipitate may be, for example, dried at 60 to 100° C., 70 to 100° C., or 80 to 100° C. for 12 to 20 hours, 14 to 20 hours, or 14 to 18 hours by means of a general drier.

The filtered coprecipitate may be fired, for example, at 400 to 800° C., 500 to 800° C., or 550 to 750° C. for 1 to 10 hours, 3 to 8 hours, or 5 to 7 hours by means of a general firing furnace.

The filtered coprecipitate may be, for example, dried at 60 to 100° C., 70 to 100° C., or 80 to 100° C. for 12 to 20 hours, 14 to 20 hours, or 14 to 18 hours by means of a general drier. In addition, the dried coprecipitate may be, for example, fired at 400 to 800° C., 500 to 800° C., or 550 to 750° C. for 1 to 10 hours, 3 to 8 hours, or 5 to 7 hours by means of a general firing furnace.

The firing may be carried out by a heat treatment method generally used in the art.

A catalyst for oxidative dehydrogenation prepared according to the method of the present invention may include, for example, a spinel ferrite ($AFe_2O_4$) and an α-iron oxide ($\alpha$-$Fe_2O_3$). Here, the α-iron oxide may be included, for example, in an amount of 15 to 80% by weight. Within this range, selectivity and yield of a conjugated diene according to oxidative dehydrogenation are superior.

In particular, the catalyst for oxidative dehydrogenation of the present invention may include an $AFe_2O_4$ structure and an $Fe_2O_3$ structure. Here, A is one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co), the content of $AFe_2O_4$ may be 38 to 85% by weight, 66 to 85% by weight, or 46 to 70% by weight, and the content of $Fe_2O_3$ may be 15 to 62% by weight, 15 to 54% by weight, or 30 to 54% by weight. Within this range, selectivity and yield of a conjugated diene according to oxidative dehydrogenation are superior.

The $AFe_2O_4$ structure may have a first peak having a maximum peak intensity in a range of 34.5° to 35.5°, a second peak having a second peak intensity in a range of 29.5° to 30.5°, and a third peak having a third peak intensity in a range of 62° to 63°, as a result of XRD analysis.

The $AFe_2O_4$ structure may be, for example, $ZnFe_2O_4$ or $MnFe_2O_4$.

The $Fe_2O_3$ structure may have a first peak having a maximum peak intensity in a range of 33° to 34°, a second peak having a second peak intensity in a range of 35° to 36°, and a third peak having a third peak intensity in a range of 53.5° to 54.5°, as a result of XRD analysis.

The $Fe_2O_3$ structure may be, for example, $\alpha$-$Fe_2O_3$.

The catalyst may have, for example, a crystallite size (D) of 50 nm or more, 60 nm or more, 70 nm or more, 50 to 80 nm, 60 to 80 nm, or 70 to 80 nm, as measured by XRD. Within this range, the activity of the catalyst is superior, the phase thereof meets the objectives of the present invention, and washing may be easily carried out.

The catalyst may have, for example, a BET surface area of 4.0 $m^2$/g or more, 4.7 $m^2$/g or more, 4.0 to 8.0 $m^2$/g, or 4.5 to 7.0 $m^2$/g, as measured by a general BET method. Within this range, the activity of the catalyst is superior.

The catalyst is applicable to a fixed bed reactor, mobile bed reactor, and fluid bed reactor for oxidative dehydrogenation, and has very broad applicability as a catalyst.

Now, the present invention will be described in more detail with reference to the following preferred examples. However, these examples are provided for illustrative purposes only. Those skilled in the art will appreciate that various modifications, additions and substitutions are possible, without departing from the scope and spirit of the invention. Therefore, it is obvious that the modifications, additions and substitutions are within the scope of the present invention.

EXAMPLE

Example 1

In step 1, 895.181 g of an aqueous metal precursor solution (at a concentration of 6.67% by weight) was prepared by dissolving 12.019 g of zinc chloride ($ZnCl_2$) and 47.662 g of ferric chloride ($FeCl_3$) in distilled water. Here, a mole ratio of the metal ingredients included in the aqueous metal precursor solution was Fe:Zn=2:1.

In step 2, a coprecipitation tank containing an aqueous ammonia solution at pH 9.5, at a concentration of 28% by weight, and at room-temperature was equipped with an outlet for the aqueous metal precursor solution and an outlet for the basic aqueous solution. An aqueous ammonia solution having the same pH and concentration as the ammonia solution in the coprecipitation tank was added to the coprecipitation tank through the basic aqueous solution outlet while adding the prepared aqueous metal precursor solution dropwise through the aqueous metal precursor solution outlet (at a dripping rate of 44.76 g/min), thereby constantly maintaining the pH of a coprecipitation solution in the coprecipitation tank at 9.5.

After completing the addition of the aqueous metal precursor solution, the coprecipitation solution was stirred for 1 hour such that sufficient coprecipitation was achieved. After stopping the stirring, a precipitate was allowed to settle for 1 hour at room temperature until the precipitate was completely settled, whereby phase separation was accomplished.

In step 3, the coprecipitation solution was vacuum-filtered by means of a vacuum filter, thereby obtaining a coprecipitate. The obtained coprecipitate was dried at 90° C. for 16 hours. The dried coprecipitate was put into a firing furnace and was thermally treated at 650° C. for 6 hours therein, thereby preparing a zinc ferrite catalyst. The contents of a spinel ferrite (ZnFe$_2$O$_4$) and α-iron oxide (α-Fe$_2$O$_3$) of the prepared zinc ferrite catalyst were respectively measured using XRD (see FIGS. 1 and 2). Results are summarized in Table 1 below.

Example 2

An experiment was carried out in the same manner as in Example 1, except that, in step 1, 8.593 g of zinc chloride (ZnCl$_2$) and 51.118 g of ferric chloride (FeCl$_3$) were dissolved in distilled water to prepare an aqueous metal precursor solution including the metal ingredients in a mole ratio of Fe:Zn=3:1, and the prepared aqueous metal precursor solution was used in an amount of 895.711. The contents of a spinel ferrite (ZnFe$_2$O$_4$) and α-iron oxide (α-Fe$_2$O$_3$) of a prepared zinc ferrite catalyst were respectively measured using XRD (see FIGS. 1 and 2). Results are summarized in Table 1 below.

Example 3

An experiment was carried out in the same manner as in Example 1, except that, in step 1, 6.686 g of zinc chloride (ZnCl$_2$) and 53.028 g of ferric chloride (FeCl$_3$) were dissolved in distilled water to prepare an aqueous metal precursor solution including the metal ingredients in a mole ratio of Fe:Zn=4:1, and the prepared aqueous metal precursor solution was used in an amount of 895.714. The contents of a spinel ferrite (ZnFe$_2$O$_4$) and α-iron oxide (α-Fe$_2$O$_3$) of a prepared zinc ferrite catalyst were respectively measured using XRD (see FIGS. 1 and 2). Results are summarized in Table 1 below.

Example 4

An experiment was carried out in the same manner as in Example 1, except that, in step 1, 5.469 g of zinc chloride (ZnCl$_2$) and 54.222 g of ferric chloride (FeCl$_3$) were dissolved in distilled water to prepare an aqueous metal precursor solution including the metal ingredients in a mole ratio of Fe:Zn=5:1, and the prepared aqueous metal precursor solution was used in an amount of 895.391. The contents of a spinel ferrite (ZnFe$_2$O$_4$) and α-iron oxide (α-Fe$_2$O$_3$) of a prepared zinc ferrite catalyst were respectively measured using XRD (see FIGS. 1 and 2). Results are summarized in Table 1 below.

Example 5

An experiment was carried out in the same manner as in Example 1, except that, in step 1, 4.998 g of zinc chloride (ZnCl$_2$) and 59.464 g of ferric chloride (FeCl$_3$) were dissolved in distilled water to prepare an aqueous metal precursor solution including the metal ingredients in a mole ratio of Fe:Zn=6:1, and the prepared aqueous metal precursor solution was used in an amount of 966.962. The contents of a spinel ferrite (ZnFe$_2$O$_4$) and α-iron oxide (α-Fe$_2$O$_3$) of a prepared zinc ferrite catalyst were respectively measured using XRD (see FIGS. 1 and 2). Results are summarized in Table 1 below.

Comparative Example 1

In step 1, 892.181 g of an aqueous metal precursor solution (at concentration of 6.69% by weight) was prepared by dissolving 12.019 g of zinc chloride (ZnCl$_2$) and 47.662 g of ferric chloride (FeCl$_3$) in distilled water. Here, a mole ratio of the metal ingredients included in the aqueous metal precursor solution was as follows: Fe:Zn=2:1.

In step 2, 70 g of an aqueous ammonia solution at a concentration of 28% by weight was added batchwise to 892.18 g of the aqueous metal precursor solution to adjust the pH of a coprecipitation solution to 9.5. After the pH of the coprecipitation solution was stabilized, a coprecipitation solution was stirred for 1 hour such that coprecipitation was sufficiently carried (pH 9.5). After stopping the stirring, a precipitate was allowed to stand for 1 hour at room temperature until the precipitate was completely sunken, whereby phase separation was accomplished.

In step 3, the coprecipitation solution was vacuum-filtered by means of a vacuum filter, thereby obtaining a coprecipitate. The obtained coprecipitate was dried at 90° C. for 16 hours. The dried coprecipitate was put into a firing furnace and was thermally treated at 650° C. for 6 hours therein, thereby preparing a zinc ferrite catalyst.

Comparative Example 2

An experiment was carried out in the same manner as in Example 1, except that, in step 1, 16.382 g of zinc chloride (ZnCl$_2$) and 43.311 g of ferric chloride (FeCl$_3$) were dissolved in distilled water to prepare an aqueous metal precursor solution including the metal ingredients in a mole ratio of Fe:Zn=2:1.5, and the prepared aqueous metal precursor solution was used in an amount of 895.393 g. The contents of a spinel ferrite (ZnFe$_2$O$_4$) and α-iron oxide (α-Fe$_2$O$_3$) of a prepared zinc ferrite catalyst were respectively measured using XRD (see FIGS. 1 and 2). Results are summarized in Table 1 below.

Comparative Example 3

An experiment was carried out in the same manner as in Example 1, except that, in step 1, 59.681 g of ferric chloride (FeCl$_3$) was merely dissolved in distilled water to prepare an aqueous metal precursor solution, and the prepared aqueous metal precursor solution was used in an amount of 895.181 g.

Comparative Example 4

A pellet-type zinc ferrite catalyst including metal ingredients in a mole ratio of Fe:Zn=2:1 (ZnFe$_2$O$_4$: 99.9%, manufactured by KOJUNDO CHEMICAL LABORATORY CO., LTD.) was used.

TABLE 1

| Classification | Fe:Zn (mole ratio) | ZnFe$_2$O$_4$ | α-Fe$_2$O$_3$ (% by weight) | ZnO |
|---|---|---|---|---|
| Example 1 | 2:1 | 85 | 15 | — |
| Example 2 | 3:1 | 70 | 30 | — |
| Example 3 | 4:1 | 52 | 48 | — |
| Example 4 | 5:1 | 46 | 54 | — |
| Example 5 | 6:1 | 38 | 62 | — |
| Comparative Example 1 | 2:1 | 86 | 14 | — |
| Comparative Example 2 | 2:1.5 | 96 | — | 4 |
| Comparative Example 3 | 1:0 | — | 100 | — |
| Comparative Example 4 | 2:1 | 100 | — | — |

Test Example

Using the catalyst for oxidative dehydrogenation prepared according to each of Examples 1 to 5 and Comparative Examples 1 to 4, butadiene was manufactured by the following method. Results are summarized in Table 2 below.

Butadiene Preparation

A mixture of 1-butene, trans-2-butene, and cis-2-butene and oxygen were used as reactants, and nitrogen and steam were additionally added together thereto. As a reactor, a metal tubular reactor was used. Ratios of reactants were determined as follows: oxygen/butene: 1, steam/butene: 4, and nitrogen/butene: 12. A gas hourly space velocity (GHSV) was set to 500 h$^{-1}$.

A fixed bed reactor was filled with the catalyst prepared according to each of the examples and the comparative examples, and the volume of a catalyst layer contacting reactants was fixed to 75 cc. Water was vaporized into steam at 150° C. by means of a vaporizer and was injected into the reactor with a butene mixture and oxygen, as reactants. The amount of the butene mixture was adjusted by means of a mass flow rate controller for liquids, addition of oxygen and nitrogen was controlled by means of a mass flow rate controller for gas, and an injection speed of steam was controlled by means of a liquid pump.

Reaction temperature was maintained at 340° C. and reaction pressure was maintained at atmospheric pressure. After reaction, a product was analyzed using gas chromatography (GC). A conversion rate of the butene mixture, a conversion rate of each butene in the mixture, selectivity of 1,3-butadiene, and a yield of 1,3-butadiene were calculated according to Mathematical Equations 1 to 3 below based on results obtained by gas chromatography.

Conversion rate (%)=(moles of reacted butene/moles of supplied butene)   [Mathematical Equation 1]

Selectivity (%)=(moles of generated 1,3-buta-diene or COx/moles of reacted butene)×100   [Mathematical Equation 2]

Yield (%)=(moles of generated 1,3-butadiene/moles of supplied butene)×100   [Mathematical Equation 3]

From Table 2, it can be confirmed that, in Examples 1 to 5 according to the present invention, all of butene conversion rate, butadiene selectivity, and yield are superior. In addition, it can be confirmed that, when a mole ratio of iron (Fe) to zinc (Zn) is increased during preparation of a catalyst, an α-iron oxide content in the catalyst increases (see Table 1), and thus, butene conversion rate, butadiene selectivity, and yield tend to increase in specific ranges. From these results, it can be confirmed that butene conversion rate, butadiene selectivity, and yield are improved by adjusting a mole ratio of zinc to iron in a predetermined range to control the phase of the zinc ferrite catalyst.

On the other hand, it can be confirmed that, in the case of Comparative Example 1 wherein a basic aqueous solution was added batchwise and a conventional method of adjusting pH of a coprecipitation solution was used, butene conversion rate, butadiene selectivity, and yield are poor despite a mole ratio of Fe:Zn being the same as in Example 1 of the present invention.

In addition, it can be confirmed that, in the case of Comparative Example 2 wherein the aqueous metal precursor solution and the basic aqueous solution were dually added according to the method of the present invention, but iron (Fe) and zinc (Zn) were mixed in a low mole ratio of about 1.33, zinc oxide was generated and, as a result, butene conversion rate, butadiene selectivity, and yield are very poor.

Further, it can be confirmed that, also in the case of Comparative Example 3 wherein a catalyst was prepared only using the aqueous iron precursor solution, butene conversion rate, butadiene selectivity, and yield are very poor. In addition, it can be confirmed that, also in the case of Comparative Example 4 wherein a pellet-type zinc ferrite catalyst generally used for oxidative dehydrogenation was used, butene conversion rate, butadiene selectivity, and yield are poor despite of a mole ratio of Fe Zn being the same as in Example 1 of the present invention.

TABLE 2

| Classification | Examples | | | | | Comparative examples | | | |
|---|---|---|---|---|---|---|---|---|---|
| | 1 | 2 | 3 | 4 | 5 | 1 | 2 | 3 | 4 |
| Mole ratio of Fe:Zn | 2:1 | 3:1 | 4:1 | 5:1 | 6:1 | 2:1 | 2:1.5 | 1:0 | 2:1 |
| Butene conversion rate | 75.26 | 75.78 | 80.32 | 80.98 | 53.63 | 57.31 | 5.23 | 27.07 | 48.36 |
| 1-butene conversion rate | 79.77 | 76.60 | 81.45 | 83.27 | 58.36 | 59.00 | 8.93 | 21.97 | 50.69 |
| Trans-2-butene conversion rate | 70.59 | 73.57 | 77.53 | 77.92 | 49.29 | 53.64 | 4.01 | 28.93 | 41.46 |
| Cis-3-butene conversion rate | 80.33 | 78.93 | 84.47 | 84.85 | 57.57 | 62.86 | 4.59 | 27.15 | 58.74 |
| 1,3-butadiene selectivity | 85.98 | 88.25 | 89.71 | 89.75 | 86.72 | 80.00 | 31.04 | 45.04 | 88.39 |
| 1,3-butadiene yield | 64.71 | 66.88 | 72.06 | 72.68 | 46.51 | 45.85 | 1.62 | 12.19 | 42.75 |

Additional Experimental Example I

Using catalysts prepared according to Example 6 and Comparative Example 5 below, butadiene was synthesized according to the aforementioned method.

Example 6

An experiment was carried out in the same manner as in Example 1, except that, in step 1, 18.5 g of manganese chloride ($MnCl_2$) and 50.7 g of ferric chloride ($FeCl_3$) were dissolved in distilled water to prepare an aqueous metal precursor solution including the metal ingredients in a mole ratio of Fe:Mn=2:1, and the prepared aqueous metal precursor solution was used in an amount of 904.7 g. Here, a butene conversion rate was 22.66%, a 1-butene conversion rate was 27.36%, a trans-2-butene conversion rate was 20.27%, a cis-2-butene conversion rate was 23.15%, a 1,3-butadiene selectivity was 28.68%, and a 1,3-butadiene yield was 6.50%.

Comparative Example 5

A pellet-type manganese ferrite catalyst including metal ingredients in a mole ratio of Fe:Mn=2:1 ($MnFe_2O_4$: 99.5%, manufactured by KOJUNDO CHEMICAL LABORATORY CO., LTD.) was used. Here, a butene conversion rate was 17.31%, a 1-butene conversion rate was 20.38%, a trans-2-butene conversion rate was 14.72%, a cis-2-butene conversion rate was 19.54%, a 1,3-butadiene selectivity was 15.22%, and a 1,3-butadiene yield was 2.63%.

As observed in Example 6 and Comparative Example 5, it can be confirmed that the catalyst prepared according to the present invention exhibits superior butene conversion rate, butadiene selectivity, and yield, compared to the pellet-type manganese ferrite catalyst having the same metal ingredient ratio generally used for oxidative dehydrogenation.

From these results, the present inventors confirmed that, when a metal oxide catalyst for oxidative dehydrogenation is prepared by a precipitation method, the pH of a coprecipitate is more stably controlled and the phase of a metal oxide catalyst prepared from the coprecipitate is controlled, by dually adding an aqueous metal oxide precursor solution and a basic aqueous solution dropwise to a coprecipitation tank containing a basic aqueous solution that has been adjusted to a specific pH, whereby a catalyst for oxidative dehydrogenation providing improved conjugated diene selectivity and yield is generated.

Additional Experimental Example II

Butadiene was synthesized as described above, except that a catalyst prepared according to Example 7 below was used and ratios of reactants among experimental conditions were set as follows: a mole ratio of oxygen/butene: 0.75, a mole ratio of steam/butene: 15, and a mole ratio of nitrogen/butene: 3. Results are summarized in Table 3 below. In addition, a catalyst prepared according to Example 1 was used to prepare butadiene under these condition for comparison with Example 7. Results are summarized in Table 3 below.

Example 7

An experiment was carried out in the same manner as in Example 1, except that, in step 1, nitrate instead of chloride, as a metal precursor, was used in the same molar amount as the chloride. A phase of a prepared catalyst was composed of 78% by weight of $ZnFe_2O_4$ and 22% by weight of $\alpha\text{-}Fe_2O_3$, a BET surface area ($m^2/g$) thereof was 4.7, and a crystallite size D*(nm) thereof was 71. On the other hand, a phase of the catalyst prepared according to Example 1 was composed of 85% $ZnFe_2O_4$ and 15% $\alpha\text{-}Fe_2O_3$, an Fe/Zn (mol/mol) ratio thereof was 2.5, a BET surface area ($m^2/g$) thereof was 6.6, and a crystallite size D*(nm) thereof was 73.

TABLE 3

| Classification | Examples | |
|---|---|---|
| | 1 | 7 |
| Mole ratio between metals | 2:1 | 2:1 |
| % by weight of $ZnFe_2O_4$ | 85 | 78 |
| % by weight of $\alpha\text{-}Fe_2O_3$ | 15 | 22 |
| % by weight of ZnO | — | — |
| Butene conversion rate | 82.9 | 81.7 |
| 1-butene conversion rate | 84.10 | 84.09 |
| Trans-2-butene conversion rate | 80.90 | 83.37 |
| Cis-3-butene conversion rate | 85.79 | 84.33 |
| 1,3-butadiene selectivity | 89.3 | 89.2 |
| 1,3-butadiene yield | 74.0 | 72.9 |

As shown in Table 3, it can be confirmed that, in the case of Example 7 in which a nitrate-based metal precursor was used instead of chloride, a butene conversion rate and a 1,3-butadiene yield are slightly decreased, compared to Example 1 wherein a chloride-based metal precursor was used.

Additional Experimental Example III

Example 8

A catalyst for oxidative dehydrogenation was prepared in the same manner as in Example 1, except that, in step 2, 28% by weight of an aqueous ammonia solution at pH 9.0 was used and the pH of a coprecipitation solution in a coprecipitation tank was maintained at 9.0. A prepared catalyst was used to synthesize butadiene in the same manner as described above, except that ratios of reactants were set as follows: a mole ratio of oxygen/butene: 0.75, a mole ratio of steam/butene: 15, and a mole ratio of nitrogen/butene: 3. Here, a butene conversion rate was 83.2%, a 1-butene conversion rate was 84.79%, a trans-2-butene conversion rate was 80.99%, a cis-3-butene conversion rate was 86.02%, a 1,3-butadiene selectivity was 90.8%, and a 1,3-butadiene yield was 75.5%. From these results, it can be confirmed that, in the case of Example 8 wherein coprecipitation was carried out at pH 9.0, a butene conversion rate and a 1,3-butadiene yield are somewhat increased, compared to Example 1 in which coprecipitation was carried out at pH 9.5.

The invention claimed is:
1. A method of preparing a catalyst for oxidative dehydrogenation, the method comprising:
  (a) preparing an aqueous precursor solution by dissolving in water a trivalent cation iron (Fe) precursor and a divalent cation zinc (Zn) precursor in a mole ratio of Fe:Zn of 3:1-5:1 and having a combined total concentration of 5 wt % to 8 wt %, wherein the trivalent cation iron (Fe) precursor and the divalent cation zinc (Zn) precursor each independently is a nitrate, an ammonium salt, a sulfate, or a chloride, wherein a pH of the aqueous precursor solution is 0 to 4;

(b) forming a coprecipitation solution by feeding dropwise, the aqueous precursor solution into an aqueous 25% to 40% by weight ammonia solution in a coprecipitation tank while constantly maintaining a pH of the coprecipitation solution by feeding an aqueous 25% to 40% by weight ammonia solution dropwise along with the aqueous precursor solution;

(c) obtaining a coprecipitate by filtering the coprecipitation solution; and (d) drying, firing, or drying and firing the coprecipitate obtained in step (c) to yield the catalyst.

2. The method according to claim 1, wherein, in step (b), the aqueous precursor solution and the aqueous ammonia solution are added dropwise from separate outlets.

3. The method according to claim 1, wherein, in step (b), the aqueous precursor solution is fed dropwise into the coprecipitation tank at a rate of 40 g/min or more.

4. The method according to claim 1, wherein, in step (b), the pH of the coprecipitation solution is maintained at greater than 8 and less than 11.

5. The method according to claim 1, wherein step (b) further comprises stirring the coprecipitation solution to which the aqueous precursor solution has been added.

6. The method according to claim 1, wherein the coprecipitate is dried in a drier at a temperature of 60° C. to 100° C. for 12 to 20 hours to yield a dried coprecipitate, and the dried coprecipitate is fired in a firing furnace at a temperature of 400° C. to 800° C. for 1 to 10 hours to yield the catalyst which contains 46% by weight $ZnFe_2O_4$ and 54% by weight $Fe_2O_3$.

7. A method of preparing a catalyst for oxidative dehydrogenation, the method comprising:

(a) preparing an aqueous precursor solution by dissolving in water a trivalent cation iron (Fe) precursor and a divalent cation metal (A) precursor containing a divalent cation metal A selected from the group consisting of copper (Cu), radium (Ra), barium (Ba), strontium (Sr), calcium (Ca), beryllium (Be), zinc (Zn), manganese (Mn), and cobalt (Co) in a mole ratio of Fe:A of 3:1 to 5:1 and having a combined total concentration of 5 wt % to 8 wt %, wherein the trivalent cation iron (Fe) precursor and the divalent cation metal (A) precursor each independently is a nitrate, an ammonium salt, a sulfate, or a chloride;

(b) forming a coprecipitation solution by feeding dropwise the aqueous precursor solution into a 28% by weight basic aqueous ammonia solution in a coprecipitation tank while constantly maintaining a pH of the coprecipitation solution by feeding a 28% by weight basic aqueous ammonia solution dropwise along with the aqueous precursor solution;

(c) obtaining a coprecipitate by filtering the coprecipitation solution; and (d) drying, firing, or drying and firing the coprecipitate obtained in step (c) to yield the catalyst.

* * * * *